(12) United States Patent
Yoon et al.

(10) Patent No.: US 11,970,700 B1
(45) Date of Patent: Apr. 30, 2024

(54) GENETIC ELEMENT E3 FOR ENHANCED INTRACELLULAR EXPRESSION OF TARGET PROTEIN ENCODED IN RNA THERAPEUTICS

(71) Applicant: INTRON BIOTECHNOLOGY, INC., Gyeonggi-do (KR)

(72) Inventors: Seong Jun Yoon, Seoul (KR); An Sung Kwon, Gyeonggi do (KR); Se Hwan Kim, Gyeonggi do (KR); Sang Hyeon Kang, Seoul (KR)

(73) Assignee: Intron Biotechnology, Inc., Gyeonggi-Do (KR)

( * ) Notice: Subject to any disclaimer, the term of this patent is extended or adjusted under 35 U.S.C. 154(b) by 0 days.

(21) Appl. No.: 18/065,194

(22) Filed: Dec. 13, 2022

(51) Int. Cl.
*C12N 15/67* (2006.01)
*C12P 21/02* (2006.01)

(52) U.S. Cl.
CPC .............. *C12N 15/67* (2013.01); *C12P 21/02* (2013.01)

(58) Field of Classification Search
CPC .................................. C12N 15/67; C12P 21/02
See application file for complete search history.

(56) References Cited

PUBLICATIONS

Alike W. van der Velden et al. Vector Design for Optimal Protein Expression (2001), vol. 31:1,7 (Year: 2001).*
EMBL Database, Accession No. LN055459. Retrieved from the internet: <URL:https://www.ebi.ac.uk/Tools/dbfetch/dbfetch?db=embl&id=LN055459&style=raw> (Year: 2014).*
EMBL Database, Accession No. HG993169. Retrieved from the internet :<URL:https://www.ebi.ac.uk/Tools/dbfetch/dbfetch?db=embl&id=HG993169&style=raw> (Year: 2021).*

* cited by examiner

*Primary Examiner* — Brian Whiteman
*Assistant Examiner* — Stephanie L Sullivan
(74) *Attorney, Agent, or Firm* — BALLARD SPAHR LLP (57) ABSTRACT

The present invention relates to an intracellular expression enhancing genetic element, which enhances the intracellular expression of target protein encoded in RNA therapeutics such as mRNA vaccines and RNA medicines. In more detail, the present invention relates to the RNA molecule which has the genetic element capable of enhancing the intracellular expression of target protein encoded in RNA therapeutics delivered into cells; the plasmid used to synthesize the RNA molecule having the genetic element "E3"; the method for synthesizing RNA molecule having the genetic element "E3" using the plasmid and utilizing the synthesized RNA molecule as RNA therapeutics.

7 Claims, 5 Drawing Sheets

Specification includes a Sequence Listing.

DNA sequence (SEQ ID NO: 1): ATGGGCAGCAGCCACCACTAT

RNA sequence (SEQ ID NO: 2): AUGGGCAGCAGCCACCACUAU

SEQUENCE LISTING

```
Sequence total quantity: 4
SEQ ID NO: 1            moltype = DNA  length = 18
FEATURE                 Location/Qualifiers
source                  1..18
                        mol_type = other DNA
                        organism = synthetic construct
SEQUENCE: 1
ggcagcagcc accactat                                                        18

SEQ ID NO: 2            moltype = RNA  length = 18
FEATURE                 Location/Qualifiers
source                  1..18
                        mol_type = other RNA
                        organism = synthetic construct
SEQUENCE: 2
ggcagcagcc accactat                                                        18

SEQ ID NO: 3            moltype = DNA  length = 7034
FEATURE                 Location/Qualifiers
source                  1..7034
                        mol_type = other DNA
                        organism = synthetic construct
SEQUENCE: 3
tcgcgcgttt cggtgatgac ggtgaaaacc tctgacacat gcagctcccg gagactgtca    60
cagcttgtct gtaagcggat gccgggagca gacaagcccg tcagggcgcg tcagcgggtg   120
ttggcgggtg tcgggctgg  cttaactatg cggcatcaga gcagattgta ctgagagtgc   180
accatatgcg gtgtgaaata ccgcacagat gcgtaaggag aaaataccgc atcaggcgcc   240
attcgccatt caggctgcgc aactgttggg aagggcgatc ggtgcgggcc tcttcgctat   300
tacgccagct ggcgaaaggg gatgtgctgc aaggcgatt  aagttgggta acgccagggt   360
tttcccagtc acgacgttgt aaaacgacgg ccagtgaatt gacgcgtatt gggatccatg   420
gtcaagcttt tggaccctcg tacagaagct aatacgactc actataggg  aataaactag   480
tattcttctg gtccccacag actcagagag aacccgccaa catgggcagc agccaccact   540
atttcgtgtt cctggtgctc ctgcctctgg tgtctagtca gtgcgtgaac ctgacgaccc   600
ggacccagct gcctccagcc tacaccaaca gcttcacccg cggcgtgtac taccccgaca   660
aggtgtttag aagctctgtg ctgcacagca cacaagacct gtttctgccc ttttttagca   720
acgtgacgtg gttccacgcc atccacgtta gcggcactaa cggcacaaag cggttcgaca   780
accccgtgct gccatttaac gacggcgtgt acttcgccag caccgaaaag tctaacatca   840
tacggggatg gatattcggc actacctgg  attccaaaac ccagagcctg ctgattgtca   900
acaacgccac caacgtggtg ataaaggtct gcgagttcca attctgcaac gaccccttcc   960
tgggcgtgta ttaccataag aacaacaaga gctggatgga aagcgagttc cgggtgtact  1020
cctccgccaa caactgtaca tttgagtacg tgtcccagcc tttcctgatg gacctggaag  1080
gcaaacaggg caactttaaa aaccttagag aattcgtgtt caagaacatc gacggctact  1140
ttaagatcta cagcaagcac accccctatca acctggtgcg ggatctgcca cagggctttt  1200
ctgccctgga acctctggtc gacctgccca tcggaatcaa catcaccagg ttccagacac  1260
tgctggccct acacagatct tacctgacac ctggagatag ctccagcggc tggaccgctg  1320
gagccgccgc ctattacgtg ggatatctgc agcctagaac attcctgctc aaatacaacg  1380
agaatggaac catcacagac gccgtggatt gcgctctgga ccctctgagc gagacaaaat  1440
gcaccctgaa gagcttcacc gttgagaagg gcatctacca gaccagcaat ttcagagtgc  1500
agcctaccga gtctatcgtg cggttcccca acatcaccaa cctgtgcccc ttcggcgagg  1560
tgttcaacgc cacccggttc gcgtccgtct acgcctggaa ccggaagaga atcagcaact  1620
gcgttgccga ctacagcgtg ctgtacaatt ctgccgcttt tctaccttc  aagtgttacg  1680
gcgtcagcc  tacaaagcta aatgacttgt gcttcacaaa cgtgtacgcc gatagctcg   1740
tgatcagagg cgacgaagtg agacagatcg cccctggcca gaccggcaag atcgccgact  1800
acaactacaa gctgcccgac gactttaccg gtgtgtgat  cgcctggaat agcaacaatc  1860
tggacagcaa ggtgggaggc aactacaact acctgtacag actgttcaga aagtctaatc  1920
tgaagccttt cgagcgggac ataagcacg  agatctacca ggccggatct acccctgca   1980
acggcgtaaa gggttttaac tgctacttcc ccctgcagtc ctacggcttc caaccaacta  2040
acggggtcgg gtaccagccc tacagagtgg tggtgctgag cttcgagctg ctgcatgccc  2100
ctgccacagt gtgcggtcct aagaaatcta ccaacctggt gaaaaacaag tgcgtgaact  2160
tcaatttcaa cggcctgacc ggcaccggag tgctgacaga atccaacaag aagttcttgc  2220
ctttccaaca gttcggacgg gatatcgccg acaccaccga cgccgtgcgc gatcctcaaa  2280
cactggaaat cctggatatc acaccctgca gcttcggcgg tgtttctgtg atcacacctg  2340
gcaccaatac cagcaatcag gtggccgtgc tgtaccagga cgtgaactgc accgaagtgc  2400
ccgtggctat tcacgctgac cagctgaccc ctacatggcg ggtgtacagc acaggctcta  2460
atgtgttcca aacaagagcc ggatgcctga tcggcgcgca gcacgtgaat agcagctacg  2520
agtgcgatat ccctatcggc gccggcatct gtgccagcta tcagactcag acaaacagca  2580
gaggcagcgc atcagcgtt  gccagccaga gcatcatcgc ttacaccatg agcctggag   2640
ccgagaacag cgtggcctat agcaacaatt ctatcgccat ccctaccaac ttcactatca  2700
gcgtgacaac agaaatcctg ccagtgtcca tgaccaagac ctcagtggac tgtaccatgt  2760
acatctgcgg cgacagcaca gaatgtagca acctgttact gcaatacggg gcttttgta   2820
cccaactgaa cagagccctg acaggcatcg ccgtggaaca ggataagaat cccaagagg   2880
tgttcgccca agtgaaacag atctataaga cccctcctat caaggacttt ggaggcttca  2940
acttcagcca gatcctgcct gaccccagca aacctagcaa gagaagcttc attgaggacc  3000
tgctgttcaa caaggtgacc ctggccgacg ccggcttcat caagcagtat ggcgactgtc  3060
tgggcgatat cgccgctaga gacctgatct gcgcccagaa attcaacggc ctgacagtgc  3120
tgcctccact gctgaccgat gagatgatcg cccagtacac ctcgccctg  ctggctggca  3180
ccatcacgtc cggctggaca tttgcgcgcc gcgctgcgct ccagatcccc ttcgccatgc  3240
agatggccta cagattcaac ggcattggcg tgactcagaa cgtgctctat gaaaaccaga  3300
```

-continued

```
agctgatcgc caatcagttc aactctgcca tcggcaagat ccaggacagc ctgtcttcta    3360
cagccagcgc cctgggcaag ctgcaggacg tggtcaacca aaacgcgcag gctcttaaca    3420
cactggtgaa gcagctgtct agcaacttcg gcgctatcag ctccgtcctg aacgatatcc    3480
tgtccagact ggaccctcct gaggccgaag tgcagatcga cagactgatc acaggcagat    3540
tgcagtccct gcaaacctac gtgacccagc agcttatccg ggccgccgag atccgggcct    3600
ctgctaacct ggctgctacc aagatgagcg agtgcgtgct gggacagagt aaacgggtcg    3660
atttctgcgg aaagggctac cacctgatgt ctttcccaca gagcgcccct cacggcgtgg    3720
tgttccttca cgtaacctac gtgccggccc aggaaaagaa ttttaccacc gcccctgcta    3780
tttgccacga tggcaaggcc cactttccaa gagagggcgt gttcgtgacg aatgaaccc     3840
actggtttgt gacccagaga aacttctacg agcctcagat catccaccac gacaacacct    3900
tcgtgagcgg caattgtgat gtggtgatcg gcatcgtgaa caataccgtg tacgacccac    3960
tgcagcccga actcgacagc ttcaaagagg aactggacaa gtacttcaag aaccacacat    4020
cacctgacgt ggacctgggc gacatctctg gcatcaacgc ctccgtggtg aatatcccaga   4080
aagagattga tagactgaat gaagtggcaa agaacctgaa cgagagcctc atcgacctgc    4140
aggagctggg caagtacgag cagtatatca agtggccttg gtacatctgg ctcggctttta   4200
tcgcgggcct gatcgctatc gtgatggtga ccatcatgct gtgttgcatg accagctgct    4260
gcagctgtct gaagggctgt tgcagctgcg gctcctgctg caagttcgac gaggatgatt    4320
ccgaacccgt cctgaagggc gtcaaactac actacacatg atgactcgag ctggtactgc    4380
atgcacgcaa tgctagctgc cccttttccg tcctgggtac cccgagtctc ccccgacctc    4440
gggtcccagg tatgctccca cctccacctg ccccactcac cacctctgct agttccagac    4500
acctcccaag cacgcagcaa tgcagctcaa aacgcttagc ctagccacac ccccacggga    4560
aacagcagtg attaacctt agcaataaac gaaagttaa ctaagctata ctaaccccag      4620
ggttggtcaa tttcgtgcca gccacaccct ggagctagca aaaaaaaaaa aaaaaaaaa    4680
aaaaaaaaaa aaaaaaaaaa aaaaaaaaag cggccgcttg gctgctgcca ccgctgagca   4740
ataactagca taacccttg gggcctctaa acgggtcttg aggggttttt tgctgaaagg    4800
aggaactata tccggattct agaatcccaa tggcgcgccg agcttggctc gagcatggtc   4860
atagctgttt cctgtgtgaa attgttatcc gctcacaatt ccacacaaca tacgagccgg   4920
aagcataaag tgtaaagcct ggggtgccta atgagtgagc taactcacat taattgcgtt   4980
gcgctcactg cccgctttcc agtcgggaaa cctgtcgtgc cagctgcatt aatgaatcgg   5040
ccaacgcgcg gggagaggcg gtttgcgtat tgggcgctct tccgcttcct cgctcactga   5100
ctcgctgcgc tcggtcgttc ggctgcggcg agcggtatca gctcactcaa aggcggtaat   5160
acggttatcc acagaatcag gggataacgc aggaaagaac atgtgagcaa aaggccagca   5220
aaaggccagg aaccgtaaaa aggccgcgtt gctggcgttt ttccataggc tccgcccccc   5280
tgacgagcat cacaaaaatc gacgctcaag tcagaggtgg cgaaacccga caggactata   5340
aagataccag gcgtttcccc ctggaagctc cctcgtgcgc tctcctgttc cgaccctgcc   5400
gcttaccgga tacctgtccg cctttctccc ttcgggaagc gtggcgcttt ctcatagctc   5460
acgctgtagg tatctcagtt cggtgtaggt cgttcgctcc aagctgggct gtgtgcacga   5520
acccccgtt cagcccgacc gctgcgcctt atccggtaac tatcgtcttg agtccaaccc    5580
ggtaagacac gacttatcgc cactggcagc agccactggt aacaggatta gcagagcgag   5640
gtatgtaggc ggtgctacag agttcttgaa gtggtggcct aactacggct acactagaag   5700
aacagtattt ggtatctgcg ctctgctgaa gccagttacc ttcggaaaaa gagttggtag   5760
ctcttgatcc ggcaaacaaa ccaccgctgg tagcggtggt ttttttgttt gcaagcagca   5820
gattacgcgc agaaaaaaag gatctcaaga agatccttt atcttttcta cggggtctga   5880
cgctcagtgg aacgaaaact cacgttaagg gattttggtc atgagattat caaaaaggat   5940
cttcacctag atccttttaa attaaaaatg aagttttaaa tcaatctaaa gtatatatga   6000
gtaaacttgg tctgacagtt agaaaactc atcgagcatc aaatgaaact gcaatttatt    6060
catatcagga ttatcaatac catatttttg aaaaagccgt ttctgtaatg aaggagaaaa   6120
ctcaccgagg cagttccata ggatggcaag atcctggtat cggtctgcga ttccgactcg   6180
tccaacatca atacaaccta ttaatttccc ctcgtcaaaa ataaggttat caagtgagaa   6240
atcaccatga gtgacgactg aatccggtga gaatggcaaa agtttatgca tttctttcca   6300
gacttgttca acaggccagc cattacgctc gtcatcaaaa tcactcgcat caaccaaacc   6360
gttattcatt cgtgattgcg cctgagcgaa acgaaatacg cgatcgctgt taaaaggaca   6420
attacaaaca ggaatcgaat gcaaccggcg caggaacact gccagcgcat caacaatatt   6480
ttcacctgaa tcaggatatt cttctaatac ctggaatgct gttttcccag ggatcgcagt   6540
ggtgagtaac catgcatcat caggagtacg gataaaatgc ttgatggtcg gaagaggcat   6600
aaattccgtc agccagttta gtctgaccat ctcatctgta acatcattgg caacgctacc   6660
tttgccatgt ttcagaaaca actctggcgc atcgggcttc ccatacaatc gatagattgt   6720
cgcacctgat tgcccgacat tatcgcgagc ccatttatac ccatataaat cagcatccat   6780
gttggaattt aatcgcggcc tagagcaaga cgtttcccgt tgaatatggc tcatactctt   6840
cctttttcaa tattattgaa gcatttatca gggttattgt ctcatgagcg gatacatatt   6900
tgaatgtatt tagaaaaata aacaaatagg ggttccgcgc acatttcccc gaaaagtgcc   6960
acctgacgtc taagaaacca ttattatcat gacattaacc tataaaaata ggcgtatcac   7020
gaggcccttt tgtc                                                      7034
```

```
SEQ ID NO: 4            moltype = DNA   length = 7016
FEATURE                 Location/Qualifiers
source                  1..7016
                        mol_type = other DNA
                        organism = synthetic construct
SEQUENCE: 4
tcgcgcgttt cggtgatgac ggtgaaaacc tctgacacat gcagctcccg gagactgtca     60
cagcttgtct gtaagcggat gccgggagca gacaagcccg tcagggcgcg tcagcgggtg    120
ttggcggggt tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt gacgcgtatt gggatccatg    420
gtcaagcttt tggaccctcg tacagaagct aatacgactc actatagggg aataaactag    480
tattcttctg gtcccacag actcagagag aacccgccac catgttcgtg ttcctggtgc    540
```

```
tcctgcctct ggtgtctagt cagtgcgtga acctgacgac ccggacccag ctgcctccag    600
cctacaccaa cagcttcacc cgcggcgtgt actaccccga caaggtgttt agaagctctg    660
tgctgcacag cacacaagac ctgtttctgc ccttttttag caacgtgaca tggttccacg    720
ccatccacgt tagcggcact aacggcacaa agcggttcga caaccccgtg ctgccattta    780
acgacggcgt gtacttcgcc agcaccgaaa agtctaacat catcgggga tggatattcg     840
gcactaccct ggattccaaa acccagagcc tgctgattgt caacaacgcc accaacgtgg    900
tgataaaggt ctgcgagttc caattctgca acgaccctt cctgggcgtg tattaccata    960
agaacaacaa gagctggatg gaaagcgagt tccgggtgta ctcctccgcc aacaactgta   1020
catttgagta cgtgtcccag cctttcctga tggacctgga aggcaaacag ggcaacttta   1080
aaaaccttag agaattcgtg ttcaagaaca tcgacggcta ctttaagatc tacagcaagc   1140
acaccctat caacctggtg cgggatctgc cacagggct ttctgccctg aacctctgg     1200
tcgacctgcc catcggaatc aacatcacca ggttccagac actgctggcc ctacacagat   1260
cttacctgac acctggagat agctccagcg gctggaccgc tggagccgcc gcctattacg   1320
tgggatatct gcagcctaga acattcctgc tcaaatacaa cgagaatgga accatcacag   1380
acgccgtgga ttgcgctctg gaccctctga gcgagacaaa atgcaccctg aagagcttca   1440
ccgttgagaa gggcatctac cagaccagca atttcagagt gcagcctacc gagtctatcg   1500
tgcggttccc caacatcacc aacctgtgcc ccttcggcga ggtgttcaac gccacccggt   1560
tcgcgtccgt ctacgcctgg aaccggaaga gaatcagcaa ctgcgttgcc gactacagcg   1620
tgctgtacaa ttctgccagc ttttctacct tcaagtgtta cggcgtcagc cctacaaagc   1680
taaatgactt gtgcttcaca aacgtgtacg ccgatagctt cgtgatcaga ggcgacgaag   1740
tgagacagat cgcccctggc cagaccggca agatcgccga ctacaactac aagctgcccg   1800
acgactttac cggttgtgtg atcgcctgga atagcaacaa ggtgacagc aaggtgggag    1860
gcaactacaa ctacctgtac agactgttca gaaagtctaa tctgaagcct ttcgagcggg   1920
acataagcac ggagatctac caggccggat ctaccccctg caacgcgta aagggtttta    1980
actgctactt ccccctgcag tcctacggct tccaaccaac taacgggtc gggtaccagc    2040
cctacagagt ggtggtgctg agcttcgagc tgctgcatgc ccctgccaca cgtgtgcggtc   2100
ctaagaaatc taccaacctg gtgaaaaaca agtgcgtgaa cttcaatttc aacggctga    2160
ccggcaccgg agtgctgaca gaatccaaca agaagttctt gcctttccaa cagttcggac   2220
gggatatcgc cgacaccacc gacgccgtgc gcgatcctca aacactggaa atcctggata   2280
tcacacctg cagcttcggc ggtgtttctg tgatcacacc tggcaccaat accagcaatc    2340
aggtggccgt gctgtaccag gacgtgaact gcaccgaagt gcccgtggct attcacgctg   2400
accagctgac ccctacatgg cgggtgtaca gcacaggctc taatgtgttc caaacaagag   2460
ccggatgcct gatcggcgcc gagcacgtga ataacagcta cgagtgcgat atccctatcg   2520
gcgccggcat ctgtgccagc tatcagactc agacaaacag cagaggcagc gcatccaccg   2580
ttgccagcca gagcatcatc gcttacacca tgagcctggg agcgagaaac agcgtggcct   2640
atagcaacaa ttctatcgcc atccctacca acttcactat cagcgtgaca acagaaatcc   2700
tgccagtgtc catgaccaag accagcgtgg actgcaccat gtacatctgc ggcgacagca   2760
cagaatgtag caacctgtta ctgcaatacg ggagcttttg tacccaactg aacagagccc   2820
tgacaggcat cgccgtggaa caggataaga ataccgagga ggtgttcgcc caagtgaaac   2880
agatctataa gacccctcct atcaaggact tggaggctt caacttcagc cagatcctgc    2940
ctgaccccag caaacctagc aagagaagct tcattgagga cctgctgttc aacaaggtga   3000
ccctggccga cgccggcttc atcaagcagt atggcgactg tctgggcgat atcgccgcta   3060
gagacctgat ctgcgcccag aaattcaacg gcctgacagt gctgcctcca ctgctgaccg   3120
atgagatgat cgcccagtac acctccgccc tgctggctgg caccatcacg tccggctgga   3180
catttggcgc cggcgctgcg ctccagatcc ccttcgccat gcagatggcc tacagattca   3240
acggcattgg cgtgactcag aacgtgctct atgaaaacca gaagctgatc gccaatcagt   3300
tcaactctgc catcggcaag atccaggaca gcctgtcttc tacagccagc gccctgggca   3360
agctgcagga cgtggtcaac caaaacgcgc aggctcttaa cacactggtg aagcagcgtg   3420
ctagcaactt cggcgctatc agctccgtcc tgaacgatat cctgtccaga ctggaccctc   3480
ctgaggccga agtgcagatc gacagactga tcacaggcag attgcagtcc ctgcaaacct   3540
acgtgaccca gcagcttatc cgggccgccg agatccggc tctgctaac ctggctgcta   3600
ccaagatgag cgagtgcgtg ctgggacaga gtaaacgggt cgatttctgc ggaaagggct   3660
accacctgat gtctttccca cagagcgccc ctcacgcgt ggtgttcctt cacgtaacct    3720
acgtgccggc ccaggaaaag aatttacca ccgcccctgc tatttgccac gatggcaagg    3780
cccactttcc aagagagggc gtgttcgtga gcaatgcact ccactggttt gtgacccaga   3840
gaaacttcta cgagcctcag atcatcacca cagacaacac cttcgtgagc ggcaattgtg   3900
atgtggtgat cggcatcgtg aacaataccg tgtacgaccc actgcagccc gaactcgaca   3960
gcttcaaaga ggaactggac aagtacttca agaaccacac atcacctgac gtggacctgg   4020
gcgacatctc tggcatcaac gcctccgtgg tgaatatcca gaaagagatt gatagactga   4080
atgaagtggc aaagaacctg aacgagagcc tcatcgacct gcaggagctg ggcaagtacg   4140
agcagtatat caagtggcct tggtacatct ggctcggctt tatcgccggc ctgatcgcta   4200
tcgtgatggt gaccatcatg ctgtgttgca tgaccagctg ctgcagctgt ctgaagggct   4260
gttgcagctg cggctcctgc tgcaagttcg acgaggatga ttccgaaccc gtcctgaagg   4320
gcgtcaaact acactgcaca tgatgactcg agctggtact aatgctaget    4380
gccccttttcc cgtcctgggt acccgagtc tccccgacc tcgggtccca ggtatgctcc    4440
cacctccacc tgcccactc accacctctg ctagttccag acacctccca agcacgcagc    4500
aatgcagctc aaaacgctta gcctagccac acccccacgg gaaacagcag tgattaacct   4560
ttagcaataa acgaaagttt aactaagcta tactaaccac agggttggtc aatttcgtgc   4620
cagccacacc ctggagctag caaaaaaaaa aaaaaaaaaa aaaaaaaaaa aaaaaaaaa    4680
aaaaaaaaaa agcggccgct ggctgctgc caccgctgag caataactag cataacccct   4740
tggggcctct aaacgggtct tgagggggttt tttgctgaaa ggaggaacta tatccggatt   4800
ctagaatccc aatggcgcgc cgagcttggc tcgagcatgg tcatagctgt ttcctgtgtg   4860
aaattgttat ccgctcacaa ttccacacaa catacgagcc ggaagcataa agtgtaaagc   4920
ctggggtgcc taatgagtga gctaactcac attaattgcg ttgcgctcac tgcccgcttt   4980
ccagtcggga aacctgtcgt gccagctgca ttaatgaatc ggccaacgcg cggggagagg   5040
cggtttgcgt attgggcgct gttccgcttc ctcgctcact gactcgctgc gctcggtcgt   5100
tcggctgcgg cgagcggtat cagctcactc aaaggcggta atacggttat ccacagaatc   5160
aggggataac gcaggaaaga acatgtgagc aaaaggccag caaaaggcca ggaaccgtaa   5220
aaaggccgcg ttgctggcgt ttttccatag gctccgcccc cctgacgagc atcacaaaaa   5280
```

```
tcgacgctca agtcagaggt ggcgaaaccc gacaggacta taaagatacc aggcgtttcc  5340
ccctggaagc tccctcgtgc gctctcctgt tccgaccctg ccgcttaccg gatacctgtc  5400
cgcctttctc ccttcgggaa gcgtggcgct ttctcatagc tcacgctgta ggtatctcag  5460
ttcggtgtag gtcgttcgct ccaagctggg ctgtgtgcac gaaccccccg ttcagcccga  5520
ccgctgcgcc ttatccggta actatcgtct tgagtccaac ccggtaagac acgacttatc  5580
gccactggca gcagccactg gtaacaggat tagcagagcg aggtatgtag gcggtgctac  5640
agagttcttg aagtggtggc ctaactacgg ctacactaga agaacagtat ttggtatctg  5700
cgctctgctg aagccagtta ccttcggaaa aagagttggt agctcttgat ccggcaaaca  5760
aaccaccgct ggtagcggtg gtttttttgt ttgcaagcag cagattacgc gcagaaaaaa  5820
aggatctcaa gaagatcctt tgatcttttc tacggggtct gacgctcagt ggaacgaaaa  5880
ctcacgttaa gggattttgg tcatgagatt atcaaaaagg atcttcacct agatcctttt  5940
aaattaaaaa tgaagtttta aatcaatcta agtatatat  gagtaaactt ggtctgacag  6000
ttagaaaaac tcatcgagca tcaaatgaaa ctgcaattta ttcatatcag gattatcaat  6060
accatatttt tgaaaaagcc gtttctgtaa tgaaggagaa aactcaccga ggcagttcca  6120
taggatggca agatcctggt atcggtctgc gattccgact cgtccaacat caatacaacc  6180
tattaatttc ccctcgtcaa aaataaggtt atcaagtgag aaatcaccat gagtgacgac  6240
tgaatccggt gagaatggca aaagtttatg catttctttc cagacttgtt caacaggcca  6300
gccattacgc tcgtcatcaa aatcactcgc atcaaccaaa ccgttattca ttcgtgattg  6360
cgcctgagcg aaacgaaata cgcgatcgct gttaaaagga caattacaaa caggaatcga  6420
atgcaaccgg cgcaggaaca ctgccagcgc atcaacaata ttttcacctg aatcaggata  6480
ttcttctaat acctggaatg ctgttttccc agggatcgca gtggtgagta accatgcatc  6540
atcaggagta cggataaaat gcttgatggt cggaagaggc ataaattccg tcagccagtt  6600
tagtctgacc atctcatctg taacatcatt ggcaacgcta cctttgccat gtttcagaaa  6660
caactctggc gcatcgggct tcccatacaa tcgatagatt gtcgcacctg attgcccgac  6720
attatcgcga gcccatttat acccatataa atcagcatcc atgttggaat ttaatcgcgg  6780
cctagagcaa gacgtttccc gttgaatatg gctcatactc ttccttttc  aatattattg  6840
aagcatttat caggggttatt gtctcatgag cggatacata tttgaatgta tttagaaaaa  6900
taaacaaata ggggttccgc gcacatttcc ccgaaaagtg ccacctgacg tctaagaaac  6960
cattattatc atgacattaa cctataaaaa taggcgtatc acgaggccct tttgtc       7016
```

GENETIC ELEMENT E3 FOR ENHANCED INTRACELLULAR EXPRESSION OF TARGET PROTEIN ENCODED IN RNA THERAPEUTICS

BACKGROUND OF THE INVENTION

Reference to Sequence Listing

The Sequence Listing submitted Dec. 13, 2022 as a text file named "mRNA_E3_ST26.xml," created on Dec. 12, 2022, and having a size of 18,087 bytes is hereby incorporated by reference pursuant to 37 C.F.R. § 1.52(e)(5).

FIELD OF THE INVENTION

The present invention relates to the enhancing genetic element ("E3" or genetic element "E3" hereinafter) for the intracellular expression of target protein encoded in RNA therapeutics such as mRNA vaccines and RNA medicines. More specifically, the present invention relates to the RNA molecule having the genetic element "E3" capable of enhancing the intracellular expression of target protein encoded in RNA molecule; the plasmid to be used to synthesize the RNA molecule having the genetic element "E3"; the method for synthesizing RNA molecule having the genetic element "E3" using the said plasmid and utilizing the synthesized RNA molecule as RNA therapeutics.

Discussion of the Related Art

RNA therapeutics constitute a rapidly expanding category of drugs. RNA therapeutics comprise two types: one type is RNA that RNA itself acts on targets such as siRNA (short interfering RNA) or miRNA (microRNA), and the other type is RNA that the protein encoded in it acts on targets such as mRNA vaccine.

In the latter type of RNA therapeutics, since the intracellular expression levels of the encoded target proteins are directly linked to the efficacy thereof, high expression levels of the encoded target proteins are desired in many cases. If the expression efficiency of the encoded target protein is high, a more excellent effect can be expected when the same amount of RNA drug is administered. In addition, since a relatively low dosage is required for the same effect, the dosage can be lowered, which can reduce drug manufacturing costs and side effects.

Particularly, as for mRNA vaccines that have been drawing increasing attention recently, the high efficiency in the intracellular expression of target proteins (i.e., antigens) is also desired. mRNA vaccines have some advantages compared to conventional vaccines such as DNA vaccines, subunit vaccines, inactivated vaccines and attenuated vaccines. First, mRNA vaccines provide relatively high safety. Because mRNA vaccines are a non-infectious, non-integrating platform distinct from DNA vaccines, there is no risk of integration into the genome of the host cell, so there is no potential risk of mutagenesis. For these reasons, the U.S. FDA does not include mRNA vaccines in the category of gene therapies unlike DNA vaccines. Also, the mRNA molecules of mRNA vaccines are decomposed by normal cellular processes. The antigen protein encoded in mRNA is only transiently produced, and foreigner mRNA molecules are normally decomposed in cytoplasm and removed shortly. Second, mRNA vaccines are beneficial in terms of efficacy. mRNA is versatile enough for easy modifications, which reinforces its stability while simultaneously improving the efficiency of translation. Also, the encapsulation of mRNA in delivery carriers enables an efficient in vivo delivery, whereby the rapid uptake into cytoplasm of target cells and the expression of target protein encoded in it is accelerated. mRNA is the minimal genetic vector; therefore, anti-vector immunity is avoided, and mRNA vaccines can be administered repeatedly. Third, mRNA vaccines are beneficial in terms of production. The mRNA molecules of mRNA vaccines are synthesized by means of in vitro transcription reaction, wherein the synthesis efficiency is high. Therefore, manufacture of mRNA vaccines is rapid, cost effective and highly scalable.

The said advantages explain the rapid advancement of mRNA vaccines. However, mRNA vaccines still need improvement in many aspects. Particularly, it is necessary to develop the technology for enhancing the efficiency of intracellular expression of target protein encoded in mRNA.

SUMMARY OF THE INVENTION

Hence, as a way of enhancing the intracellular expression of target proteins encoded in RNA therapeutics, the present inventors intend to provide the genetic element "E3", which is placed adjacent to the 5'-end of the target protein-coding sequence and capable of enhancing the intracellular expression of target proteins, and also a method for synthesizing the RNA molecules having the genetic element "E3" and using the synthesized RNA molecules as RNA therapeutics.

Figure 1:
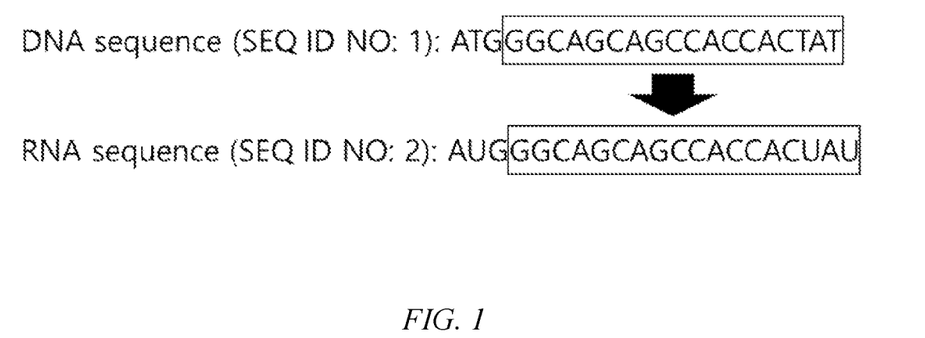
FIG. 1 illustrates the relationship between DNA sequence set forth in SEQ ID NO: 1 and RNA sequence set forth in SEQ ID NO: 2.

Thus, the first object of the present invention is to provide the DNA sequence set forth in SEQ ID NO: 1 of the genetic element "E3", which is placed adjacent to the 5'-end of the target protein-coding sequence and capable of enhancing the intracellular expression of target proteins encoded in RNA molecules. The DNA sequence set forth in SEQ ID NO: 1 for the said genetic element "E3" is presented based on the sequence of plasmid to be used for the synthesis of RNA molecules having the genetic element "E3", and FIG. 1 is given as a reference for understanding it.

The other object of the present invention is to provide a method for synthesizing RNA molecules having the genetic element "E3" using the plasmid having nucleotide sequence set forth in SEQ ID NO: 1 and utilizing the synthesized RNA molecules as RNA therapeutics including mRNA vaccines.

To achieve the said objects, the inventors of the present invention have discovered the genetic element "E3" that is placed adjacent to the 5'-end of the target protein sequence encoded in RNA molecules and capable of enhancing the intracellular expression of the encoded target protein, developed the plasmid having the said genetic element "E3", and synthesized the RNA molecules using the said plasmid, introduced the synthesized RNA molecules into cells, and demonstrated the effect of genetic element "E3" in the enhanced intracellular expression of the target protein in comparison to that when the genetic element "E3" of the present invention is not applied, thereby completing the present invention.

Thus, according to a first aspect of the present invention, the present invention provides the RNA sequence of the genetic element "E3" which is placed adjacent to the 5'-end of the target protein sequence encoded in RNA molecules and capable of enhancing the intracellular expression of the target protein. To be specific, the present invention provides the nucleotide sequence set forth in SEQ ID NO: 1, which is presented as the sequence on the plasmid (see FIG. 1).

It is obvious that the nucleotide sequence set forth in SEQ ID NO: 1 can be partially modified by a person skilled in the art using existing technology. The said modification includes the partial substitution of the nucleotide sequence, partial addition to the nucleotide sequence, and partial deletion of the nucleotide sequence. Nevertheless, it is most desirable to use the nucleotide sequence set forth in SEQ ID NO: 1 disclosed in the present invention.

According to a second aspect of the present invention, the present invention provides the RNA molecules, which functionally enhance the intracellular expression of the target protein encoded in RNA molecules, comprising the following genetic factors and arrangement:
a) 5'-untranslated region (UTR) sequence,
b) Sequence AUG corresponding to translation initiation codon,
c) Enhancing genetic element "E3" RNA sequence set forth in SEQ ID NO: 2
d) Target protein-coding sequence placed adjacent to the 3'-end of the said enhancing genetic element "E3" RNA sequence set forth in SEQ ID NO: 2,
e) 3'-untranslated region (UTR) sequence, and
f) Poly U sequence.

Wherein, the said Poly U sequence is 20-200 nucleotides in length.

According to a third aspect of the present invention, the present invention provides a method for placing the genetic element "E3" DNA sequence set forth in SEQ ID NO: 1 into the plasmid to be used for RNA synthesis, synthesizing the RNA molecules having the enhancing genetic element "E3" RNA sequence set forth in SEQ ID NO: 2, using the said plasmid, and utilizing the synthesized RNA molecules having the genetic element "E3" as RNA therapeutics. The present invention provides an example of an application as mRNA vaccines. However, the present invention may well be applied to other RNA therapeutics without limit.

According to a fourth aspect of the present invention, the plasmid of the present invention comprises a) 5'-untranslated region (UTR) sequence, b) translation initiation codon ATG, c) genetic element "E3" DNA sequence set forth in SEQ ID NO: 1, d) target-protein coding sequence placed adjacent to the 3'-end of the said genetic element "E3" DNA sequence set forth in SEQ ID NO: 1, e) 3'-untranslated region (UTR) sequence, and f) Poly A sequence, which are placed in the said order.

Wherein, the said Poly A sequence is 20-200 nucleotides in length.

According to a fifth aspect of the present invention, the present invention provides a method for synthesizing the RNA molecules having the genetic element "E3" using the plasmid comprising a) 5'-untranslated region (UTR) sequence, b) translation initiation codon ATG, c) genetic element "E3" DNA sequence set forth in SEQ ID NO: 1, d) target protein-coding sequence placed adjacent to the 3'-end of the said genetic element "E3" DNA sequence set forth in SEQ ID NO: 1, e) 3'-untranslated region (UTR) sequence, and f) Poly A sequence, which are placed in the said order, and utilizing the synthesized RNA molecules as RNA therapeutics.

Wherein, the said Poly A sequence is 20-200 nucleotides in length.

Advantageous Effects of Invention

If using the RNA molecule having the RNA sequence set forth in SEQ ID NO: 2 which is synthesized with the plasmid having the DNA sequence set forth in SEQ ID NO: 1, as an RNA therapeutics, the expression level of target protein encoded in the RNA molecule can be enhanced, making it possible to obtain a higher intracellular expression level of the target protein without increasing the doses of RNA therapeutics, thereby enhancing the effects from same amount of RNA therapeutics, and reducing drug manufacturing costs and side effects since a relatively low dosage is required for the same effect.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings:

FIG. 4 is the experimental results showing that the RNA (test group) synthesized using the plasmid having the nucleotide sequence set forth in SEQ ID NO: 1 is superior to conventional RNA (control group) synthesized using the plasmid not having the nucleotide sequence set forth in SEQ ID NO: 1 in the intracellular expression level of the target protein. (A) Representative result of western blotting. Lane M is the protein size marker; Lane 1 is the expression level of the target protein in the control group; Lane 2 is the expression level of the target protein in the test group. (B) Efficiency of target protein expression comparatively analyzed in triplicate. "Case 1" uses the conventional RNA (control group); and "Case 2" uses the RNA synthesized using the plasmid having the nucleotide sequence set forth in SEQ ID NO: 1 (test group).

DETAILED DESCRIPTION OF THE ILLUSTRATED EMBODIMENTS

Hereinafter, the present invention is described in more detail on the basis of the Embodiments, which however constitute only some examples of the present invention, not limiting the applicability thereof.

Example 1: Construction and Linearization of Plasmid to be Used for Synthesizing RNA Molecule Having Genetic Element "E3" for Enhancing the Intracellular Expression of Target Protein First, the plasmid SARS-CoV-2-Spike-E3_pUC-GW-Kan shown in FIG. 2 was constructed using the gene synthesis technology (the nucleotide sequence of the constructed plasmid is presented in SEQ ID NO: 3).

Figure 2:
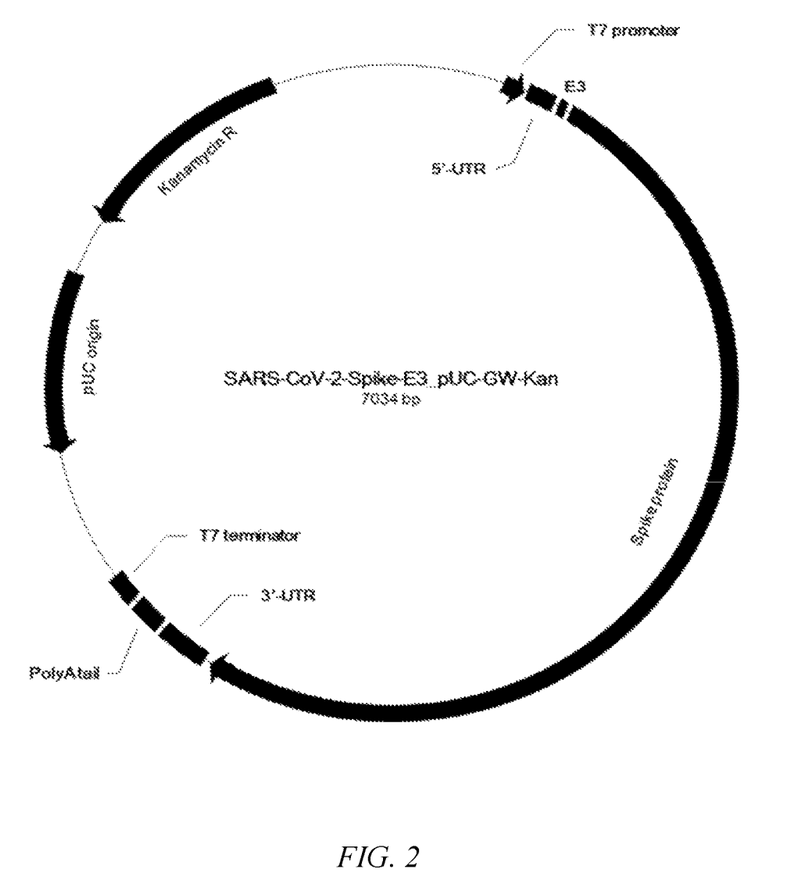
FIG. 2 illustrates an example of plasmid to be used for synthesizing RNA molecule having the enhancing genetic element "E3" RNA sequence set forth in SEQ ID NO: 2.

Specifically, the constructed plasmid SARS-CoV-2-Spike-E3_pUC-GW-Kan has in order the 5'-UTR (untranslated region) sequence, the genetic element "E3" for enhancing the target protein carrying the DNA sequence set forth in SEQ ID NO: 1 right behind the initiation codon of coronavirus spike protein gene, the sequence encoding the coronavirus spike protein as the target protein-coding sequence, 3'-UTR sequence and Poly A sequence.

Large amount of the constructed plasmid was prepared by introducing the constructed plasmid into *E. coli*. Specifically, the plasmid SARS-CoV-2-Spike-E3_pUC-GW-Kan was introduced into *E. coli* (DH5α strain) and the transformant was cultivated in a Luria-Bertani broth containing 50 µg/ml kanamycin. After overnight cultivation, a conventional plasmid large-preparation was conducted.

The circular plasmid SARS-CoV-2-Spike-E3_pUC-GW-Kan prepared in the said process underwent the restriction enzyme treatment for its linearization and then the linearized plasmid was purified. Specifically, the prepared circular plasmid SARS-CoV-2-Spike-E3_pUC-GW-Kan was treated with the restriction enzyme NotI (37° C., 16 hours) to cleave the site right behind the end of Poly A tail sequence, and the linearized plasmid was purified using a conventional phenol/chloroform extraction. The linearized plasmid prepared was used as a DNA template for the in vitro transcription reaction for RNA synthesis.

Figure 3:
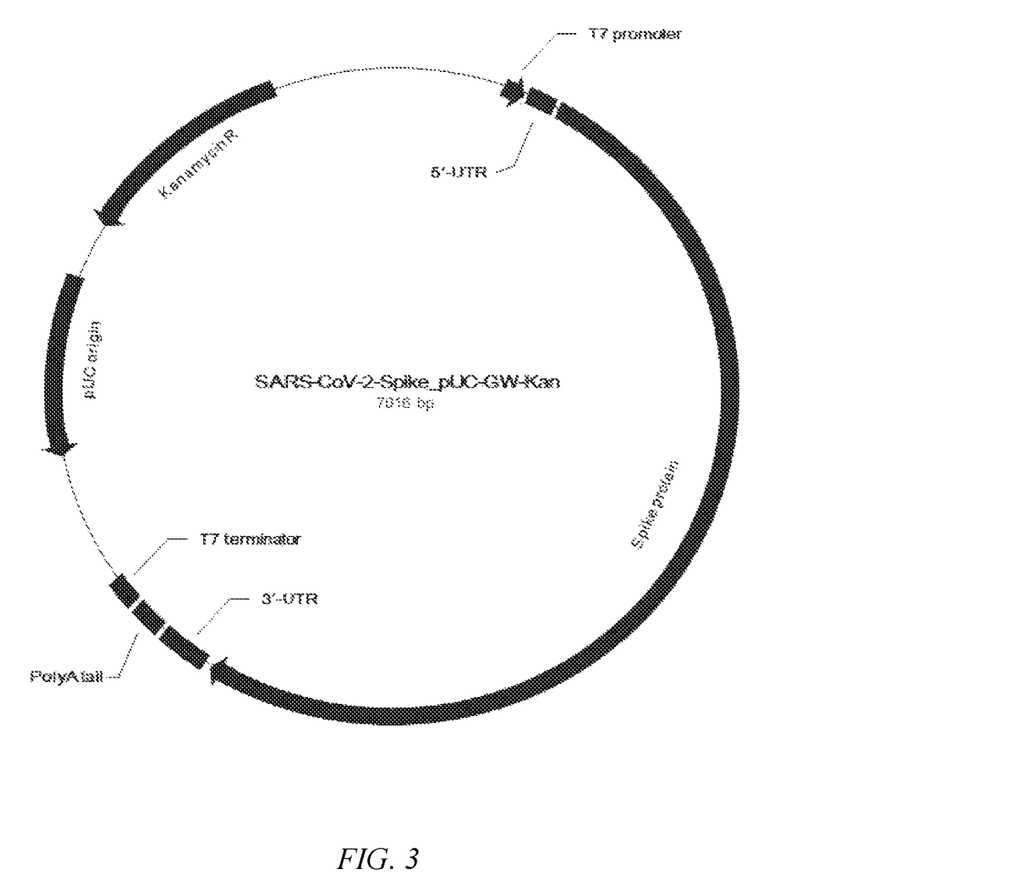
FIG. 3 illustrates an example of plasmid to be used for synthesizing RNA molecule not having the enhancing genetic element "E3" RNA sequence set forth in SEQ ID NO: 2.

Similarly, the linearized control plasmid SARS-CoV-2-Spike_pUC-GW-Kan was prepared, and used as a template for the in vitro transcription reaction for the synthesizing the control RNA. The plasmid map for the control plasmid is shown in FIG. 3, and the nucleotide sequence of the control plasmid is presented in SEQ ID NO: 4.

Example 2: mRNA Synthesis Using In Vitro Transcription

The test mRNA having the genetic element "E3" set forth in SEQ ID NO: 2 and the control mRNA not containing the genetic element "E3" set forth in SEQ ID NO: 2 were synthesized via the in vitro transcription reaction using the linearized plasmid prepared in Example 1 as a DNA template. In the synthesis reaction of the test mRNA, the linearized plasmid SARS-CoV-2-Spike-E3_pUC-GW-Kan was used as a DNA template, whereas the linearized plasmid SARS-CoV-2-Spike_pUC-GW-Kan was used as a DNA template in the synthesis reaction of the control mRNA. Specifically, this experiment comprises the following steps.

In the in vitro transcription reaction, a mixture of nucleotide triphosphates (NTP) was used, wherein the NTP mixture may contain chemically modified NTP, natural NTP, or a mixture of natural NTP and chemically modified NTP.

To synthesize the test mRNA and the control mRNA via the in vitro transcription reaction, the HiScribe™ T7 High Yield RNA Synthesis Kit (New England Biolabs) was used. The reaction components for the in vitro transcription reaction are shown in Table 1 below.

TABLE 1

| Components | Volume (µl) | Concentration |
| --- | --- | --- |
| DNA template | 5 | 0.2 µg/µl |
| 10× reaction buffer | 2 | |
| ATP (100 mM) | 2 | 10 mM |
| GTP (100 mM) | 2 | 10 mM |
| UTP (100 mM) | 2 | 10 mM |
| CTP (100 mM) | 2 | 10 mM |
| T7 RNA polymerase mix | 2 | |
| DEPC-treated water | 3 | |
| Total volume | 20 | |

The in vitro transcription reaction was performed at 37° C. for 2 hours. Following the in vitro transcription reaction, the reaction mixture was stored overnight at 4° C. for the next-day purification or immediately used for the RNA purification. For the RNA purification, firstly to decompose the DNA template included in the reaction mixture, 5 units of RNase-free DNase I was added to the reaction mixture and then the reaction mixture was incubated at 37° C. for 30 minutes. Following the treatment with DNase I, the RNA was purified using the Monarch® RNA Cleanup Kit (New England Biolabs) according to the manufacturer's instruction. Quantification of the purified RNA was performed using the NanoDrop (Thermo Fisher Scientific). Also, the proper size and integrity of RNA was confirmed by agarose gel electrophoresis.

Next, the purified RNA underwent the capping and 2'-O-methylation. For the reaction, the Vaccinia Capping Enzyme and 2'-O-Methyltransferase were used according to the manufacturer's (New England Biolabs) instruction. Specifically, firstly, the purified uncapped RNA was mixed with the DEPC-treated water until the final volume reached 13.5 µl. The mixture was kept at 65° C. for 5 minutes to denature the RNA molecules, and immediately chilled in an ice-bath. Then, the denatured RNA was mixed with 10× capping buffer (2.0 µl), 10 mM GTP (1.0 µl), 4 mM S-adenosylmethionine (SAM, 1.0 µl), RNase inhibitor (20 units, 0.5 µl), Vaccinia Capping Enzyme (10 units, 1.0 µl) and 2'-O-Methyltransferase (50 units, 1.0 µl), and then the mixture was incubated at 37° C. for 1 hour. The capped RNA was purified using the Monarch® RNA Cleanup Kit (New England Biolabs) according to the manufacturer's instruction. Following the purification, quantification of RNA was performed using the NanoDrop (Thermo Fisher Scientific). Lastly, the proper size and integrity of RNA was confirmed by agarose gel electrophoresis.

Example 3: Comparing the Efficiency of Intracellular Target Protein Expression

The intracellular expression of the target protein (antigen in this Example) was compared using the test mRNA which has the genetic element "E3" placed adjacent to the 5'-end of the target protein according to the present invention, and also the corresponding control mRNA which does not have the genetic element "E3". Both the test and control mRNA were prepared in Example 2.

Specifically, firstly, HeLa cells were cultured in a cell culture dish (900) to be used for the introduction of RNA into the cells. The cells were harvested by treating with trypsin. Then, cells were seeded per well on a 24-well plate to be $2 \times 10^5$ cells/well. Following the cell seeding, the 2 µg RNA prepared in Example 2 was introduced into the HeLa cells using the commercial transfection reagent (Lipofectamine™ MessengerMAX™, Invitrogen) according to the manufacturer's instruction. At 12 hours after the intracellular introduction, the cell lysate was secured to examine the intracellular expression of the target protein using a conventional western blotting. The 1:1000 dilution of rabbit anti-SARS Spike c-terminal (Abcam) and the mouse anti-rabbit IgG-HRP were used as the primary and secondary antibodies for the western blotting, respectively.

Figure 4:
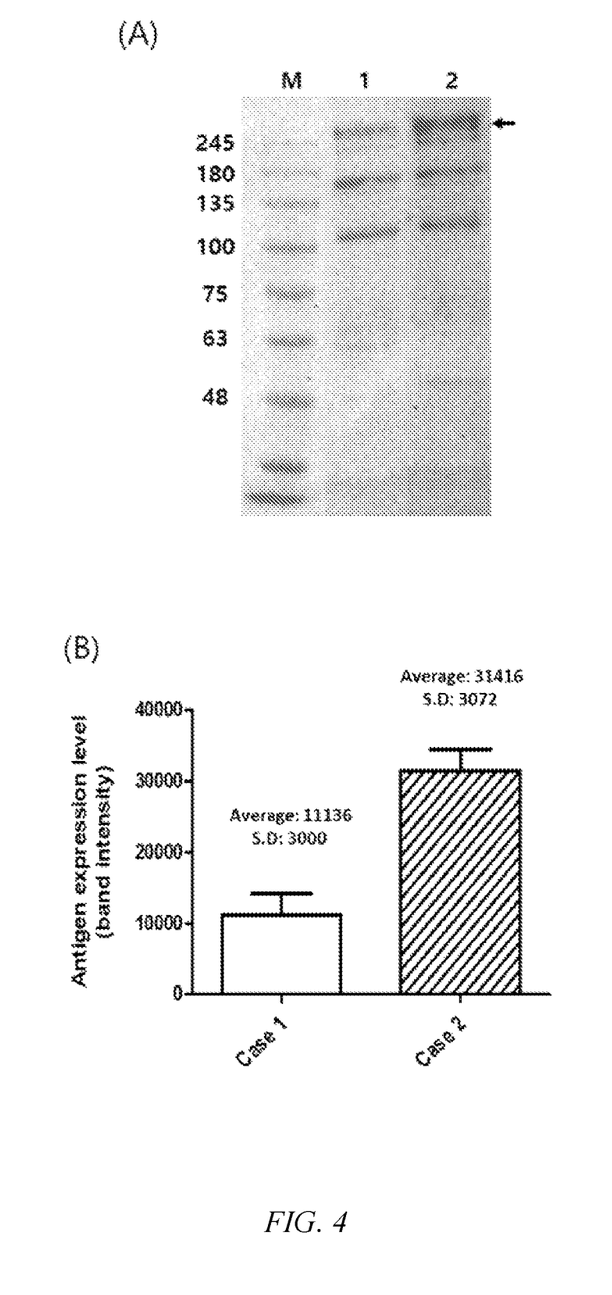
Figure 5:
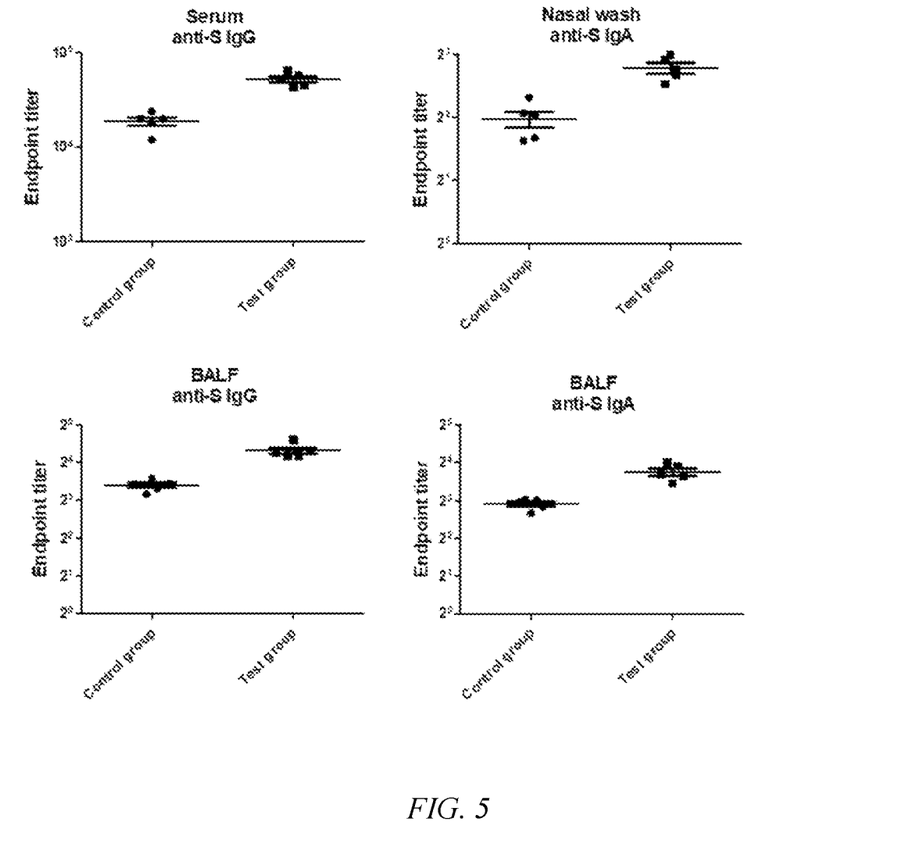
FIG. 5 is the experimental results of immune response elicited vaccination with the SARS-CoV-2 mucosal mRNA vaccine prepared using conventional mRNA (control group) and mRNA having the genetic element "E3" (test group).

As results of triplicate experiments to compare the efficiency of the intracellular expression of the target protein between the test and control mRNA, the test mRNA exhibited improved efficiency of the intracellular expression of the target protein by approximately 300% compared with the control mRNA (FIG. 4).

The said experimental result demonstrated the effects of the genetic element "E3" in enhancing the efficiency of the intracellular expression of the target protein according to the present invention. That is, the present invention was found to be effectively applicable to some cases wherein high intracellular expressions of target proteins are required.

Example 4: Application to mRNA Vaccine

The target protein of the RNA prepared in Example 2 is SARS-CoV-2 antigen. Therefore, the RNA prepared in Example 2 is applicable as mRNA vaccines.

In this Example, the effects of the present invention when applied to mRNA vaccine was investigated using the RNA molecules prepared in Example 2 with the technology held by the inventors of the present invention.

As the test and control mRNA, the mRNA used as the test and control mRNA in Example 3 were used, respectively. The control and test vaccine samples for the animal test were prepared in the same method. For reference, only the manufacture of the test vaccine sample is given below.

The test vaccine sample (E3_LNP-P-1/2, hereinafter) was manufactured by encapsulating the test mRNA in peptide-conjugated lipid nanoparticles (LNP). The peptides P1 and P2 conjugated to lipid nanoparticles here were synthesized by a specialized company.

The terminal residue of the peptides P1 and P2 is cysteine, which was coupled to the maleimide group of the PEG-lipid [1,2-distearoyl-sn-glycero-3-phosphoethanolamine-N-[maleimide(polyethylene glycol)-2000] to manufacture the peptide-conjugated PEG-lipid for use in the peptide-conjugated LNP manufacturing. To briefly describe the coupling of the peptides with the maleimide group of PEG-lipid, the peptides P1 and P2 were dissolved in water (1:1 mole ratio), while the PEG-lipid was dissolved in dimethylformamide (DMF). Here, the mole ratio between the total peptide and PEG-lipid was 1.2:1. The prepared peptide solution and the prepared PEG-lipid solution were mixed together, and the mixture was agitated at 4° C. for 18 hours. To remove any uncoupled peptides, the reaction mixture was dialyzed against 2 L water for at least 18 hours. Upon completion of the dialysis, the peptide-conjugated PEG-lipid was recovered via ultrafiltration using Amicon ultra centrifugal filters (Merck Millipore, MWCO: 3K) and then the filtrate was subjected to diafiltration using 70% ethanol. The prepared peptide-conjugated PEG-lipid was kept at −20° C. until use.

Using the peptide-conjugated PEG-lipid prepared in the said process, the E3_LNP-P-1/2 was manufactured as follows. Using the NanoAssemblr microfluidic device (Precision Nanosystems), the lipid components dissolved in ethanol (including the peptide-conjugated PEG-lipid) were mixed with the test mRNA dissolved in 50 mM sodium citrate buffer solution (pH 4.0). The mole percentages of the lipid components comprised 50% DLin-MC3-DMA (ionizable cationic lipid), 10% DSPC, 38.5% cholesterol and 1.5% peptide-conjugated PEG-lipid. The lipid component solution (ethanol phase) and the test mRNA solution (aqueous phase) were assembled in the microfluidic device at 1:3 flow rate. The total assembled flow rate was 12 ml/minutes per microfluidic cartridge. The manufactured peptide-conjugated LNP sample was dialyzed against phosphate-buffered saline (PBS, pH 7.2) for at least 18 hours using a Slide-A-Lyzer™ dialysis cassettes (Thermo Fisher Scientific). The E3_LNP-P-1/2 sample obtained through the dialysis was concentrated using Amicon ultra centrifugal filters (Merck Millipore), and then finally filtrated using 0.22 μm filters. The final obtained E3_LNP-P-1/2 solution was kept at −20° C. until use.

The control vaccine sample was manufactured according to the same method as described above using the control mRNA instead of the test mRNA. The control vaccine sample manufactured was named LNP-P-1/2.

Using the prepared test and control vaccine sample, we conducted the animal test as follows. 5-week-old female C57BL/6 mice were used as the test animal. All mice were bred and raised in a specific pathogen free (SPF) facility. The mice were assigned the following groups and underwent the nasal administration of the vaccine sample. The control vaccine sample LNP-P-1/2 was administered to the control group (C) nasally (10 μg mRNA), whereas the test vaccine sample E3_LNP-P-1/2 was administered to the test group (T) nasally (10 μg mRNA). The nasal administration was conducted twice, in Week 0 and Week 3. For the nasal administration, each mouse was placed in a gas chamber and anesthetized with isoflurane. After a short while, the anesthetized mouse was taken out of the gas chamber and placed in supine position. The nasal administration of the vaccine sample was performed using a P20 pipette fitted with a gel loading tip. After nasal administration, the mouse was laid back inside the gas chamber in supine position. This procedure was repeated for the next animal in sequence.

15 days after the second nasal administration, the sera, nasal wash and bronchoalveolar lavage fluid (BALF) were collected to evaluate the effectiveness of the vaccination. Then, protease inhibitor was added to the collected sera, nasal wash and BALF, which were subsequently kept at −80° C.

The titer of anti-spike protein antibody included in the collected sera, nasal wash and BALF was analyzed using the ELISA. Specifically, 1 μg/ml spike protein diluted in PBS was coated onto ELISA plates overnight at 4° C. or for 2 hours at 37° C. Then, the ELISA plate was blocked at room temperature for 2 hours with the blocking buffer (PBS+1% BSA+0.1% Tween-20). After washing of ELISA plate, the collected sera, nasal wash and BALF samples were added at different dilutions. The detection was performed using commercially available ELISA kit. For detection, horseradish peroxidase (HRP)-conjugated anti-mouse IgG (1:5,000 dilution) and HRP-conjugated anti-mouse IgA (1:10,000 dilution) were used. The results are presented in FIG. 5. As shown in FIG. 5, the result indicates the mucosal mRNA vaccine based on the RNA having the genetic element "E3" for enhancing the intracellular expression of the target protein in the present invention provides a higher level of systemic and mucosal immunity compared with the existing mRNA vaccine (control vaccine sample).

Based on the said result, the mRNA vaccine manufactured according to the present invention provides the superior efficacy of the conventional mRNA vaccine.

Notwithstanding the detailed description of the specific aspects of the present invention, those skilled in the art will recognize, or be able to ascertain the description involves no more than desirable Examples of the present invention. Hence, the scope of the present invention is not intended to be limited to the description above, but rather is as set forth in the following claims and their equivalents.

SEQUENCES

GGCAGCAGCCACCACTAT [SEQ ID NO: 1]

GGCAGCAGCCACCACUAU [SEQ ID NO: 2]

[SEQ ID NO: 3]
```
   1 TCGCGCGTTT CGGTGATGAC GGTGAAAACC TCTGACACAT GCAGCTCCCG GAGACTGTCA
  61 CAGCTTGTCT GTAAGCGGAT GCCGGGAGCA GACAAGCCCG TCAGGGCGCG TCAGCGGGTG
 121 TTGGCGGGTG TCGGGGCTGG CTTAACTATG CGGCATCAGA GCAGATTGTA CTGAGAGTGC
 181 ACCATATGCG GTGTGAAATA CCGCACAGAT GCGTAAGGAG AAAATACCGC ATCAGGCGCC
 241 ATTCGCCATT CAGGCTGCGC AACTGTTGGG AAGGGCGATC GGTGCGGGCC TCTTCGCTAT
 301 TACGCCAGCT GGCGAAAGGG GGATGTGCTG CAAGGCGATT AAGTTGGGTA ACGCCAGGGT
 361 TTTCCCAGTC ACGACGTTGT AAAACGACGG CCAGTGAATT GACGCGTATT GGGATCCATG
 421 GTCAAGCTTT TGGACCCTCG TACAGAAGCT AATACGACTC ACTATAGGGG AATAAACTAG
 481 TATTCTTCTG GTCCCCACAG ACTCAGAGAG AACCCGCCAC CATGGGCAGC AGCCACCACT
 541 ATTTCGTGTT CCTGGTGCTC CTGCCTCTGG TGTCTAGTCA GTGCGTGAAC CTGACGACCC
 601 GGACCCAGCT GCCTCCAGCC TACACCAACA GCTTCACCCG CGGCGTGTAC TACCCCGACA
 661 AGGTGTTTAG AAGCTCTGTG CTGCACAGCA CACAAGACCT GTTTCTGCCC TTTTTTAGCA
 721 ACGTGACATG GTTCCACGCC ATCCACGTTA GCGGCACTAA CGGCACAAAG CGGTTCGACA
 781 ACCCCGTGCT GCCATTTAAC GACGGCGTGT ACTTCGCCAG CACCGAAAAG TCTAACATCA
 841 TACGGGGATG GATATTCGGC ACTACCCTGG ATTCCAAAAC CCAGAGCCTG CTGATTGTCA
 901 ACAACGCCAC CAACGTGGTG ATAAAGGTCT GCGAGTTCCA ATTCTGCAAC GACCCCTTCC
 961 TGGGCGTGTA TTACCATAAG AACAACAAGA GCTGGATGGA AAGCGAGTTC CGGGTGTACT
1021 CCTCCGCCAA CAACTGTACA TTTGAGTACG TGTCCCAGCC TTTCCTGATG GACCTGGAAG
1081 GCAAACAGGG CAACTTTAAA AACCTTAGAG AATTCGTGTT CAAGAACATC GACGGCTACT
1141 TTAAGATCTA CAGCAAGCAC ACCCCTATCA ACCTGGTGCG GGATCTGCCA CAGGGCTTTT
1201 CTGCCCTGGA ACCTCTGGTC GACCTGCCCA TCGGAATCAA CATCACCAGG TTCCAGACAC
1261 TGCTGGCCCT ACACAGATCT TACCTGACAC CTGGAGATAG CTCCAGCGGC TGGACCGCTG
1321 GAGCCGCCGC CTATTACGTG GGATATCTGC AGCCTAGAAC ATTCCTGCTC AAATACAACG
1381 AGAATGGAAC CATCACAGAC GCCGTGGATT GCGCTCTGGA CCCTCTGAGC GAGACAAAAT
1441 GCACCCTGAA GAGCTTCACC GTTGAGAAGG GCATCTACCA GACCAGCAAT TTCAGAGTGC
1501 AGCCTACCGA GTCTATCGTG CGGTTCCCCA ACATCACCAA CCTGTGCCCC TTCGGCGAGG
1561 TGTTCAACGC CACCCGGTTC GCGTCCGTCT ACGCCTGGAA CCGGAAGAGA ATCAGCAACT
1621 GCGTTGCCGA CTACAGCGTG CTGTACAATT CTGCCAGCTT TTCTACCTTC AAGTGTTACG
1681 GCGTCAGCCC TACAAAGCTA AATGACTTGT GCTTCACAAA CGTGTACGCC GATAGCTTCG
1741 TGATCAGAGG CGACGAAGTG AGACAGATCG CCCCTGGCCA GACCGGCAAG ATCGCCGACT
1801 ACAACTACAA GCTGCCCGAC GACTTTACCG GTTGTGTGAT CGCCTGGAAT AGCAACAATC
1861 TGGACAGCAA GGTGGGAGGC AACTACAACT ACCTGTACAG ACTGTTCAGA AAGTCTAATC
1921 TGAAGCCTTT CGAGCGGGAC ATAAGCACGG AGATCTACCA GGCCGGATCT ACCCCCTGCA
1981 ACGGCGTAAA GGGTTTTAAC TGCTACTTCC CCCTGCAGTC CTACGGCTTC CAACCAACTA
2041 ACGGGGTCGG GTACCAGCCC TACAGAGTGG TGGTGCTGAG CTTCGAGCTG CTGCATGCCC
2101 CTGCCACAGT GTGCGGTCCT AAGAAATCTA CCAACCTGGT GAAAACAAG TGCGTGAACT
```

-continued

```
2161 TCAATTTCAA CGGCCTGACC GGCACCGGAG TGCTGACAGA ATCCAACAAG AAGTTCTTGC
2221 CTTTCCAACA GTTCGGACGG GATATCGCCG ACACCACCGA CGCCGTGCGC GATCCTCAAA
2281 CACTGGAAAT CCTGGATATC ACACCCTGCA GCTTCGGCGG TGTTTCTGTG ATCACACCTG
2341 GCACCAATAC CAGCAATCAG GTGGCCGTGC TGTACCAGGA CGTGAACTGC ACCGAAGTGC
2401 CCGTGGCTAT TCACGCTGAC CAGCTGACCC CTACATGGCG GGTGTACAGC ACAGGCTCTA
2461 ATGTGTTCCA AACAAGAGCC GGATGCCTGA TCGGCGCCGA GCACGTGAAT AACAGCTACG
2521 AGTGCGATAT CCCTATCGGC GCCGGCATCT GTGCCAGCTA TCAGACTCAG ACAAACAGCA
2581 GAGGCAGCGC ATCCAGCGTT GCCAGCCAGA GCATCATCGC TTACACCATG AGCCTGGGAG
2641 CCGAGAACAG CGTGGCCTAT AGCAACAATT CTATCGCCAT CCCTACCAAC TTCACTATCA
2701 GCGTGACAAC AGAAATCCTG CCAGTGTCCA TGACCAAGAC CAGCGTGGAC TGCACCATGT
2761 ACATCTGCGG CGACAGCACA GAATGTAGCA ACCTGTTACT GCAATACGGG AGCTTTTGTA
2821 CCCAACTGAA CAGAGCCCTG ACAGGCATCG CCGTGGAACA GGATAAGAATACCCAAGAGG
2881 TGTTCGCCCA AGTGAAACAG ATCTATAAGA CCCCTCCTAT CAAGGACTTT GGAGGCTTCA
2941 ACTTCAGCCA GATCCTGCCT GACCCCAGCA AACCTAGCAA GAGAAGCTTC ATTGAGGACC
3001 TGCTGTTCAA CAAGGTGACC CTGGCCGACG CCGGCTTCAT CAAGCAGTAT GGCGACTGTC
3061 TGGGCGATAT CGCCGCTAGA GACCTGATCT GCGCCCAGAA ATTCAACGGC CTGACAGTGC
3121 TGCCTCCACT GCTGACCGAT GAGATGATCG CCCAGTACAC CTCCGCCCTG CTGGCTGGCA
3181 CCATCACGTC CGGCTGGACA TTTGGCGCCG GCGCTGCGCT CCAGATCCCC TTCGCCATGC
3241 AGATGGCCTA CAGATTCAAC GGCATTGGCG TGACTCAGAA CGTGCTCTAT GAAAACCAGA
3301 AGCTGATCGC CAATCAGTTC AACTCTGCCA TCGGCAAGAT CCAGGACAGC CTGTCTTCTA
3361 CAGCCAGCGC CCTGGGCAAG CTGCAGGACG TGGTCAACCA AAACGCGCAG GCTCTTAACA
3421 CACTGGTGAA GCAGCTGTCT AGCAACTTCG GCGCTATCAG CTCCGTCCTG AACGATATCC
3481 TGTCCAGACT GGACCCTCCT GAGGCCGAAG TGCAGATCGA CAGACTGATC ACAGGCAGAT
3541 TGCAGTCCCT GCAAACCTAC GTGACCCAGC AGCTTATCCG GGCCGCCGAG ATCCGGGCCT
3601 CTGCTAACCT GGCTGCTACC AAGATGAGCG AGTGCGTGCT GGGACAGAGT AAACGGGTCG
3661 ATTTCTGCGG AAAGGGCTAC CACCTGATGT CTTTCCCACA GAGCGCCCCT CACGGCGTGG
3721 TGTTCCTTCA CGTAACCTAC GTGCCGGCCC AGGAAAAGAA TTTTACCACC GCCCCTGCTA
3781 TTTGCCACGA TGGCAAGGCC CACTTTCCAA GAGAGGGCGT GTTCGTGAGC AATGGAACCC
3841 ACTGGTTTGT GACCCAGAGA AACTTCTACG AGCCTCAGAT CATCACCACA GACAACACCT
3901 TCGTGAGCGG CAATTGTGAT GTGGTGATCG GCATCGTGAA CAATACCGTG TACGACCCAC
3961 TGCAGCCCGA ACTCGACAGC TTCAAAGAGG AACTGGACAA GTACTTCAAG AACCACACAT
4021 CACCTGACGT GGACCTGGGC GACATCTCTG GCATCAACGC CTCCGTGGTG AATATCCAGA
4081 AAGAGATTGA TAGACTGAAT GAAGTGGCAA AGAACCTGAA CGAGAGCCTC ATCGACCTGC
4141 AGGAGCTGGG CAAGTACGAG CAGTATATCA AGTGGCCTTG GTACATCTGG CTCGGCTTTA
4201 TCGCCGGCCT GATCGCTATC GTGATGGTGA CCATCATGCT GTGTTGCATG ACCAGCTGCT
4261 GCAGCTGTCT GAAGGGCTGT TGCAGCTGCG GCTCCTGCTG CAAGTTCGAC GAGGATGATT
4321 CCGAACCCGT CCTGAAGGGC GTCAAACTAC ACTACACATG ATGACTCGAG CTGGTACTGC
4381 ATGCACGCAA TGCTAGCTGC CCCTTTCCCG TCCTGGGTAC CCCGAGTCTC CCCCGACCTC
4441 GGGTCCCAGG TATGCTCCCA CCTCCACCTG CCCCACTCAC CACCTCTGCT AGTTCCAGAC
4501 ACCTCCCAAG CACGCAGCAA TGCAGCTCAA AACGCTTAGC CTAGCCACAC CCCCACGGGA
```

-continued

```
4561 AACAGCAGTG ATTAACCTTT AGCAATAAAC GAAAGTTTAA CTAAGCTATA CTAACCCCAG

4621 GGTTGGTCAA TTTCGTGCCA GCCACACCCT GGAGCTAGCA AAAAAAAAAAAAAAAAAAA

4681 AAAAAAAAAA AAAAAAAAAAAAAAAAAAAGCGGCCGCTTG GCTGCTGCCACCGCTGAGCA

4741 ATAACTAGCA TAACCCCTTG GGGCCTCTAA ACGGGTCTTG AGGGGTTTTT TGCTGAAAGG

4801 AGGAACTATA TCCGGATTCT AGAATCCCAA TGGCGCGCCG AGCTTGGCTC GAGCATGGTC

4861 ATAGCTGTTT CCTGTGTGAA ATTGTTATCC GCTCACAATT CCACACAACA TACGAGCCGG

4921 AAGCATAAAG TGTAAAGCCT GGGGTGCCTA ATGAGTGAGC TAACTCACAT TAATTGCGTT

4981 GCGCTCACTG CCCGCTTTCC AGTCGGGAAA CCTGTCGTGC CAGCTGCATT AATGAATCGG

5041 CCAACGCGCG GGGAGAGGCG GTTTGCGTAT TGGGCGCTGT TCCGCTTCCT CGCTCACTGA

5101 CTCGCTGCGC TCGGTCGTTC GGCTGCGGCG AGCGGTATCA GCTCACTCAA AGGCGGTAAT

5161 ACGGTTATCC ACAGAATCAG GGGATAACGC AGGAAAGAACATGTGAGCAAAAGGCCAGCA

5221 AAAGGCCAGG AACCGTAAAA AGGCCGCGTT GCTGGCGTTT TTCCATAGGC TCCGCCCCCC

5281 TGACGAGCAT CACAAAAATC GACGCTCAAG TCAGAGGTGG CGAAACCCGACAGGACTATA

5341 AAGATACCAG GCGTTTCCCC CTGGAAGCTC CCTCGTGCGC TCTCCTGTTC CGACCCTGCC

5401 GCTTACCGGA TACCTGTCCG CCTTTCTCCC TTCGGGAAGC GTGGCGCTTT CTCATAGCTC

5461 ACGCTGTAGG TATCTCAGTT CGGTGTAGGT CGTTCGCTCC AAGCTGGGCT GTGTGCACGA

5521 ACCCCCCGTT CAGCCCGACC GCTGCGCCTT ATCCGGTAAC TATCGTCTTG AGTCCAACCC

5581 GGTAAGACAC GACTTATCGC CACTGGCAGC AGCCACTGGT AACAGGATTA GCAGAGCGAG

5641 GTATGTAGGC GGTGCTACAG AGTTCTTGAA GTGGTGGCCT AACTACGGCT ACACTAGAAG

5701 AACAGTATTT GGTATCTGCG CTCTGCTGAA GCCAGTTACC TTCGGAAAAA GAGTTGGTAG

5761 CTCTTGATCC GGCAAACAAA CCACCGCTGG TAGCGGTGGT TTTTTTGTTT GCAAGCAGCA

5821 GATTACGCGC AGAAAAAAAG GATCTCAAGA AGATCCTTTG ATCTTTTCTA CGGGGTCTGA

5881 CGCTCAGTGG AACGAAAACT CACGTTAAGG GATTTTGGTC ATGAGATTAT CAAAAAGGAT

5941 CTTCACCTAG ATCCTTTTAA ATTAAAAATG AAGTTTTAAA TCAATCTAAA GTATATATGA

6001 GTAAACTTGG TCTGACAGTT AGAAAAACTC ATCGAGCATC AAATGAAACT GCAATTTATT

6061 CATATCAGGA TTATCAATAC CATATTTTTG AAAAAGCCGT TTCTGTAATG AAGGAGAAAA

6121 CTCACCGAGG CAGTTCCATA GGATGGCAAG ATCCTGGTAT CGGTCTGCGA TTCCGACTCG

6181 TCCAACATCA ATACAACCTA TTAATTTCCC CTCGTCAAAA ATAAGGTTAT CAAGTGAGAA

6241 ATCACCATGA GTGACGACTG AATCCGGTGA GAATGGCAAA AGTTTATGCA TTTCTTTCCA

6301 GACTTGTTCA ACAGGCCAGC CATTACGCTC GTCATCAAAA TCACTCGCAT CAACCAAACC

6361 GTTATTCATT CGTGATTGCG CCTGAGCGAA ACGAAATACG CGATCGCTGT TAAAAGGACA

6421 ATTACAAACA GGAATCGAAT GCAACCGGCG CAGGAACACT GCCAGCGCAT CAACAATATT

6481 TTCACCTGAA TCAGGATATT CTTCTAATAC CTGGAATGCT GTTTTCCCAG GGATCGCAGT

6541 GGTGAGTAAC CATGCATCAT CAGGAGTACG GATAAAATGC TTGATGGTCG GAAGAGGCAT

6601 AAATTCCGTC AGCCAGTTTA GTCTGACCAT CTCATCTGTA ACATCATTGG CAACGCTACC

6661 TTTGCCATGT TTCAGAAACA ACTCTGGCGC ATCGGGCTTC CCATACAATC GATAGATTGT

6721 CGCACCTGAT TGCCCGACAT TATCGCGAGC CCATTTATAC CCATATAAAT CAGCATCCAT

6781 GTTGGAATTT AATCGCGGCC TAGAGCAAGA CGTTTCCCGT TGAATATGGC TCATACTCTT

6841 CCTTTTTCAA TATTATTGAA GCATTATCA GGGTTATTGT CTCATGAGCG ATACATATT

6901 TGAATGTATT TAGAAAAATA AACAAATAGG GGTTCCGCGC ACATTTCCCC GAAAAGTGCC

6961 ACCTGACGTC TAAGAAACCA TTATTATCAT GACATTAACC TATAAAAATA GGCGTATCAC
```

-continued

```
7021 GAGGCCCTTT TGTC
```

[SEQ ID NO: 4]
```
   1 TCGCGCGTTT CGGTGATGAC GGTGAAAACC TCTGACACAT GCAGCTCCCG GAGACTGTCA
  61 CAGCTTGTCT GTAAGCGGAT GCCGGGAGCA GACAAGCCCG TCAGGGCGCG TCAGCGGGTG
 121 TTGGCGGGTG TCGGGCTGG CTTAACTATG CGGCATCAGA GCAGATTGTA CTGAGAGTGC
 181 ACCATATGCG GTGTGAAATA CCGCACAGAT GCGTAAGGAG AAAATACCGC ATCAGGCGCC
 241 ATTCGCCATT CAGGCTGCGC AACTGTTGGG AAGGGCGATC GGTGCGGGCC TCTTCGCTAT
 301 TACGCCAGCT GGCGAAAGGG GGATGTGCTG CAAGGCGATT AAGTTGGGTA ACGCCAGGGT
 361 TTTCCCAGTC ACGACGTTGT AAAACGACGG CCAGTGAATT GACGCGTATT GGGATCCATG
 421 GTCAAGCTTT TGGACCCTCG TACAGAAGCT AATACGACTC ACTATAGGGG AATAAACTAG
 481 TATTCTTCTG GTCCCCACAG ACTCAGAGAG AACCCGCCAC CATGTTCGTG TTCCTGGTGC
 541 TCCTGCCTCT GGTGTCTAGT CAGTGCGTGA ACCTGACGAC CCGGACCCAG CTGCCTCCAG
 601 CCTACACCAA CAGCTTCACC CGCGGCGTGT ACTACCCCGA CAAGGTGTTT AGAAGCTCTG
 661 TGCTGCACAG CACACAAGAC CTGTTTCTGC CCTTTTTTAG CAACGTGACA TGGTTCCACG
 721 CCATCCACGT TAGCGGCACT AACGGCACAA AGCGGTTCGA CAACCCCGTG CTGCCATTTA
 781 ACGACGGCGT GTACTTCGCC AGCACCGAAA AGTCTAACAT CATACGGGGA TGGATATTCG
 841 GCACTACCCT GGATTCCAAA ACCCAGAGCC TGCTGATTGT CAACAACGCC ACCAACGTGG
 901 TGATAAAGGT CTGCGAGTTC CAATTCTGCA ACGACCCCTT CCTGGGCGTG TATTACCATA
 961 AGAACAACAA GAGCTGGATG GAAAGCGAGT TCCGGGTGTA CTCCTCCGCC AACAACTGTA
1021 CATTTGAGTA CGTGTCCCAG CCTTTCCTGA TGGACCTGGA AGGCAAACAG GGCAACTTTA
1081 AAAACCTTAG AGAATTCGTG TTCAAGAACA TCGACGGCTA CTTTAAGATC TACAGCAAGC
1141 ACACCCCTAT CAACCTGGTG CGGGATCTGC CACAGGGCTT TTCTGCCCTG GAACCTCTGG
1201 TCGACCTGCC CATCGGAATC AACATCACCA GGTTCCAGAC ACTGCTGGCC CTACACAGAT
1261 CTTACCTGAC ACCTGGAGAT AGCTCCAGCG GCTGGACCGC TGGAGCCGCC GCCTATTACG
1321 TGGGATATCT GCAGCCTAGA ACATTCCTGC TCAAATACAA CGAGAATGGA ACCATCACAG
1381 ACGCCGTGGA TTGCGCTCTG GACCCTCTGA GCGAGACAAA ATGCACCCTG AAGAGCTTCA
1441 CCGTTGAGAA GGGCATCTAC CAGACCAGCA ATTTCAGAGT GCAGCCTACC GAGTCTATCG
1501 TGCGGTTCCC CAACATCACC AACCTGTGCC CCTTCGGCGA GGTGTTCAAC GCCACCCGGT
1561 TCGCGTCCGT CTACGCCTGG AACCGGAAGA GAATCAGCAA CTGCGTTGCC GACTACAGCG
1621 TGCTGTACAA TTCTGCCAGC TTTTCTACCT TCAAGTGTTA CGGCGTCAGC CCTACAAAGC
1681 TAAATGACTT GTGCTTCACA AACGTGTACG CCGATAGCTT CGTGATCAGA GGCGACGAAG
1741 TGAGACAGAT CGCCCCTGGC CAGACCGGCA AGATCGCCGA CTACAACTAC AAGCTGCCCG
1801 ACGACTTTAC CGGTTGTGTG ATCGCCTGGA ATAGCAACAA TCTGGACAGC AAGGTGGGAG
1861 GCAACTACAA CTACCTGTAC AGACTGTTCA GAAAGTCTAA TCTGAAGCCT TTCGAGCGGG
1921 ACATAAGCAC GGAGATCTAC CAGGCCGGAT CTACCCCCTG CAACGGCGTA AAGGGTTTTA
1981 ACTGCTACTT CCCCCTGCAG TCCTACGGCT TCCAACCAAC TAACGGGGTC GGGTACCAGC
2041 CCTACAGAGT GGTGGTGCTG AGCTTCGAGC TGCTGCATGC CCCTGCCACA GTGTGCGGTC
2101 CTAAGAAATC TACCAACCTG GTGAAAAACA AGTGCGTGAA CTTCAATTTC AACGGCCTGA
2161 CCGGCACCGG AGTGCTGACA GAATCCAACA AGAAGTTCTT GCCTTTCCAA CAGTTCGGAC
2221 GGGATATCGC CGACACCACC GACGCCGTGC GCGATCCTCA AACACTGGAA ATCCTGGATA
2281 TCACACCCTG CAGCTTCGGC GGTGTTTCTG TGATCACACC TGGCACCAAT ACCAGCAATC
```

-continued

```
2341 AGGTGGCCGT GCTGTACCAG GACGTGAACT GCACCGAAGT GCCCGTGGCT ATTCACGCTG
2401 ACCAGCTGAC CCCTACATGG CGGGTGTACA GCACAGGCTC TAATGTGTTC CAAACAAGAG
2461 CCGGATGCCT GATCGGCGCC GAGCACGTGA ATAACAGCTA CGAGTGCGAT ATCCCTATCG
2521 GCGCCGGCAT CTGTGCCAGC TATCAGACTC AGACAAACAG CAGAGGCAGC GCATCCAGCG
2581 TTGCCAGCCA GAGCATCATC GCTTACACCA TGAGCCTGGG AGCCGAGAAC AGCGTGGCCT
2641 ATAGCAACAA TTCTATCGCC ATCCCTACCA ACTTCACTAT CAGCGTGACA ACAGAAATCC
2701 TGCCAGTGTC CATGACCAAG ACCAGCGTGG ACTGCACCAT GTACATCTGC GGCGACAGCA
2761 CAGAATGTAG CAACCTGTTA CTGCAATACG GGAGCTTTTG TACCCAACTG AACAGAGCCC
2821 TGACAGGCAT CGCCGTGGAA CAGGATAAGA ATACCCAAGA GGTGTTCGCC CAAGTGAAAC
2881 AGATCTATAA GACCCCTCCT ATCAAGGACT TTGGAGGCTT CAACTTCAGC CAGATCCTGC
2941 CTGACCCCAG CAAACCTAGC AAGAGAAGCT TCATTGAGGA CCTGCTGTTC AACAAGGTGA
3001 CCCTGGCCGA CGCCGGCTTC ATCAAGCAGT ATGGCGACTG TCTGGGCGAT ATCGCCGCTA
3061 GAGACCTGAT CTGCGCCCAG AAATTCAACG GCCTGACAGT GCTGCCTCCA CTGCTGACCG
3121 ATGAGATGAT CGCCCAGTAC ACCTCCGCCC TGCTGGCTGG CACCATCACG TCCGGCTGGA
3181 CATTTGGCGC CGGCGCTGCG CTCCAGATCC CCTTCGCCAT GCAGATGGCC TACAGATTCA
3241 ACGGCATTGG CGTGACTCAG AACGTGCTCT ATGAAAACCA GAAGCTGATC GCCAATCAGT
3301 TCAACTCTGC CATCGGCAAG ATCCAGGACA GCCTGTCTTC TACAGCCAGC GCCCTGGGCA
3361 AGCTGCAGGA CGTGGTCAAC CAAAACGCGC AGGCTCTTAA CACACTGGTG AAGCAGCTGT
3421 CTAGCAACTT CGGCGCTATC AGCTCCGTCC TGAACGATAT CCTGTCCAGA CTGGACCCTC
3481 CTGAGGCCGA AGTGCAGATC GACAGACTGA TCACAGGCAG ATTGCAGTCC CTGCAAACCT
3541 ACGTGACCCA GCAGCTTATC CGGGCCGCCG AGATCCGGGC CTCTGCTAAC CTGGCTGCTA
3601 CCAAGATGAG CGAGTGCGTG CTGGGACAGA GTAAACGGGT CGATTTCTGC GGAAAGGGCT
3661 ACCACCTGAT GTCTTTCCCA CAGAGCGCCC CTCACGGCGT GGTGTTCCTT CACGTAACCT
3721 ACGTGCCGGC CCAGGAAAAG AATTTTACCA CCGCCCCTGC TATTTGCCAC GATGGCAAGG
3781 CCCACTTTCC AAGAGAGGGC GTGTTCGTGA GCAATGGAAC CCACTGGTTT GTGACCCAGA
3841 GAAACTTCTA CGAGCCTCAG ATCATCACCA CAGACAACAC CTTCGTGAGC GGCAATTGTG
3901 ATGTGGTGAT CGGCATCGTG AACAATACCG TGTACGACCC ACTGCAGCCC GAACTCGACA
3961 GCTTCAAAGA GGAACTGGAC AAGTACTTCA AGAACCACAC ATCACCTGAC GTGGACCTGG
4021 GCGACATCTC TGGCATCAAC GCCTCCGTGG TGAATATCCA GAAAGAGATT GATAGACTGA
4081 ATGAAGTGGC AAAGAACCTG AACGAGAGCC TCATCGACCT GCAGGAGCTG GGCAAGTACG
4141 AGCAGTATAT CAAGTGGCCT TGGTACATCT GGCTCGGCTT TATCGCCGGC CTGATCGCTA
4201 TCGTGATGGT GACCATCATG CTGTGTTGCA TGACCAGCTG CTGCAGCTGT CTGAAGGGCT
4261 GTTGCAGCTG CGGCTCCTGC TGCAAGTTCG ACGAGGATGA TTCCGAACCC GTCCTGAAGG
4321 GCGTCAAACT ACACTACACA TGATGACTCG AGCTGGTACT GCATGCACGC AATGCTAGCT
4381 GCCCCTTTCC CGTCCTGGGT ACCCCGAGTC TCCCCCGACC TCGGGTCCCA GGTATGCTCC
4441 CACCTCCACC TGCCCCACTC ACCACCTCTG CTAGTTCCAG ACACCTCCCA AGCACGCAGC
4501 AATGCAGCTC AAAACGCTTA GCCTAGCCAC ACCCCCACGG GAAACAGCAG TGATTAACCT
4561 TTAGCAATAA ACGAAAGTTT AACTAAGCTA TACTAACCCC AGGGTTGGTC AATTTCGTGC
4621 CAGCCACACCCTGGAGCTAGCAAAAAAAAAAAAAAAAAAAAAAAAAAAA AAAAAAAAA
4681 AAAAAAAAAA AGCGGCCGCT TGGCTGCTGC CACCGCTGAG CAATAACTAG CATAACCCCT
```

```
4741 TGGGGCCTCT AAACGGGTCT TGAGGGGTTT TTTGCTGAAA GGAGGAACTA TATCCGGATT

4801 CTAGAATCCC AATGGCGCGC CGAGCTTGGC TCGAGCATGG TCATAGCTGT TTCCTGTGTG

4861 AAATTGTTAT CCGCTCACAA TTCCACACAA CATACGAGCC GGAAGCATAA AGTGTAAAGC

4921 CTGGGGTGCC TAATGAGTGA GCTAACTCAC ATTAATTGCG TTGCGCTCAC TGCCCGCTTT

4981 CCAGTCGGGA AACCTGTCGT GCCAGCTGCA TTAATGAATC GGCCAACGCG CGGGGAGAGG

5041 CGGTTTGCGT ATTGGGCGCT GTTCCGCTTC CTCGCTCACT GACTCGCTGC GCTCGGTCGT

5101 TCGGCTGCGG CGAGCGGTAT CAGCTCACTC AAAGGCGGTA ATACGGTTAT CCACAGAATC

5161 AGGGGATAAC GCAGGAAAGA ACATGTGAGC AAAAGGCCAGCAAAAGGCCAGGAACCGTAA

5221 AAAGGCCGCG TTGCTGGCGT TTTTCCATAG GCTCCGCCCC CCTGACGAGC ATCACAAAAA

5281 TCGACGCTCA AGTCAGAGGT GGCGAAACCC GACAGGACTA TAAAGATACC AGGCGTTTCC

5341 CCCTGGAAGC TCCCTCGTGC GCTCTCCTGT TCCGACCCTG CCGCTTACCG GATACCTGTC

5401 CGCCTTTCTC CCTTCGGGAA GCGTGGCGCT TTCTCATAGC TCACGCTGTA GGTATCTCAG

5461 TTCGGTGTAG GTCGTTCGCT CCAAGCTGGG CTGTGTGCAC GAACCCCCCG TTCAGCCCGA

5521 CCGCTGCGCC TTATCCGGTA ACTATCGTCT TGAGTCCAAC CCGGTAAGAC ACGACTTATC

5581 GCCACTGGCA GCAGCCACTG GTAACAGGAT TAGCAGAGCG AGGTATGTAG GCGGTGCTAC

5641 AGAGTTCTTG AAGTGGTGGC CTAACTACGG CTACACTAGA AGAACAGTAT TTGGTATCTG

5701 CGCTCTGCTG AAGCCAGTTA CCTTCGGAAA AAGAGTTGGT AGCTCTTGAT CCGGCAAACA

5761 AACCACCGCT GGTAGCGGTG GTTTTTTTGT TTGCAAGCAG CAGATTACGC GCAGAAAAAA

5821 AGGATCTCAA GAAGATCCTT TGATCTTTTC TACGGGGTCT GACGCTCAGT GGAACGAAAA

5881 CTCACGTTAA GGGATTTTGG TCATGAGATT ATCAAAAAGG ATCTTCACCT AGATCCTTTT

5941 AAATTAAAAA TGAAGTTTTA AATCAATCTA AAGTATATAT GAGTAAACTT GGTCTGACAG

6001 TTAGAAAAAC TCATCGAGCA TCAAATGAAA CTGCAATTTA TTCATATCAG GATTATCAAT

6061 ACCATATTTT TGAAAAAGCC GTTTCTGTAA TGAAGGAGAA AACTCACCGA GGCAGTTCCA

6121 TAGGATGGCA AGATCCTGGT ATCGGTCTGC GATTCCGACT CGTCCAACAT CAATACAACC

6181 TATTAATTTC CCCTCGTCAA AAATAAGGTT ATCAAGTGAG AAATCACCAT GAGTGACGAC

6241 TGAATCCGGT GAGAATGGCA AAAGTTTATG CATTTCTTTC CAGACTTGTT CAACAGGCCA

6301 GCCATTACGC TCGTCATCAA AATCACTCGC ATCAACCAAA CCGTTATTCA TTCGTGATTG

6361 CGCCTGAGCG AAACGAAATA CGCGATCGCT GTTAAAAGGA CAATTACAAA CAGGAATCGA

6421 ATGCAACCGG CGCAGGAACA CTGCCAGCGC ATCAACAATA TTTTCACCTG AATCAGGATA

6481 TTCTTCTAAT ACCTGGAATG CTGTTTTCCC AGGGATCGCA GTGGTGAGTA ACCATGCATC

6541 ATCAGGAGTA CGGATAAAAT GCTTGATGGT CGGAAGAGGC ATAAATTCCG TCAGCCAGTT

6601 TAGTCTGACC ATCTCATCTG TAACATCATT GGCAACGCTA CCTTTGCCAT GTTTCAGAAA

6661 CAACTCTGGC GCATCGGGCT TCCCATACAA TCGATAGATT GTCGCACCTG ATTGCCCGAC

6721 ATTATCGCGA GCCCATTTAT ACCCATATAA ATCAGCATCC ATGTTGGAAT TTAATCGCGG

6781 CCTAGAGCAA GACGTTTCCC GTTGAATATG GCTCATACTC TTCCTTTTTC AATATTATTG

6841 AAGCATTTAT CAGGGTTATT GTCTCATGAG CGGATACATA TTTGAATGTA TTTAGAAAAA

6901 TAAACAAATA GGGGTTCCGC GCACATTTCC CCGAAAAGTG CCACCTGACG TCTAAGAAAC

6961 CATTATTATC ATGACATTAA CCTATAAAAA TAGGCGTATC ACGAGGCCCT TTCGTC
```

What is claimed is:

1. An mRNA molecule having a sequence that functionally enhances the intracellular expression of an encoded target protein, comprising
   a) a 5'-untranslated region (UTR) sequence,
   b) an AUG sequence for translation initiation,
   c) an enhancing genetic element RNA sequence as set forth in SEQ ID NO: 2,
   d) a target protein-coding sequence placed adjacent to the 3'-end of the said enhancing genetic element RNA sequence as set forth in SEQ ID NO: 2,
   e) a 3'-untranslated region (UTR) sequence, and
   f) a poly U sequence.

2. The mRNA molecule of claim 1, the said Poly U sequence comprises 20-200 nucleotides in length.

3. The mRNA molecule of claim 1, the RNA molecule is a mRNA vaccine or RNA medicine.

4. A plasmid comprising the arrangement in order of a) a 5' untranslated region (UTR) sequence, b) an ATG sequence, c) an enhancing genetic element DNA sequence set forth in SEQ ID NO: 1, d) a target protein-coding sequence placed adjacent to 3'-end of the said enhancing genetic element DNA sequence set forth in SEQ ID NO: 1, e) a 3'-untranslated region (UTR) sequence, and f) a poly A sequence.

5. The plasmid of claim 4, the said poly A sequence comprises 20-200 nucleotides in length.

6. A method for RNA molecule synthesis comprising: RNA molecule synthesis comprising:
   introducing, to a cell, a plasmid comprising the arrangement in order of a) a 5'-untranslated region (UTR) sequence, b) a translation initiation codon ATG, c) an enhancing genetic element DNA sequence set forth in SEQ ID NO: 1, d) a target protein-coding sequence placed adjacent to 3'-end of the said enhancing genetic element DNA sequence set forth in SEQ ID NO: 1, e) a 3'-untranslated region (UTR) sequence, and f) a poly A sequence, and
   incubating the cell for sufficient time to allow for in vitro transcription of a RNA molecule transcribed from the plasmid, thereby synthesizing the RNA molecule.

7. The method of claim 6, wherein the said poly A sequence comprises 20-200 nucleotides in length.

* * * * *